United States Patent [19]

Suga

[11] 4,232,971
[45] Nov. 11, 1980

[54] INTEGRATING SPHERE TYPE STANDARD LIGHT SOURCE DEVICE

[76] Inventor: Shigeru Suga, 20-2, Yoyogi 5-chome, Shibuya-ku, Tokyo, Japan

[21] Appl. No.: 23,094

[22] Filed: Mar. 22, 1979

[30] Foreign Application Priority Data

Mar. 23, 1978 [JP] Japan ............................ 53-036113[U]

[51] Int. Cl.$^3$ .......................... G01N 21/47; G01J 1/00
[52] U.S. Cl. .................................... 356/446; 356/402; 356/236; 250/228
[58] Field of Search ............... 356/445, 446, 447, 448, 356/402, 236; 250/228

[56] References Cited

U.S. PATENT DOCUMENTS 2,325,350   7/1943   West ............................... 356/236 X Primary Examiner—Vincent P. McGraw
Attorney, Agent, or Firm—Wenderoth, Lind & Ponack

[57] ABSTRACT

An integrating sphere type standard light source has a spherical shell the inner surface of which is coated with a white coating having a high reflectivity. The shell has a light source aperture in the top thereof, a viewing aperture in the side thereof and a specimen exposure aperture in the bottom thereof. A light source is mounted in the light source aperture and depends into said shell and includes a source of light and a light shielding plate between the source of light and the remainder of the interior of the shell, the light shielding plate also being coated with a white coating having a high reflectivity. A specimen supporting plate is positioned beneath the specimen exposure aperture and is normally positioned for supporting a specimen at the bottommost point of an imaginary spherical surface which is an extension of the internal surface of the shell into the specimen exposure aperture. A specimen supporting plate is mounted for movement into and out of the normal position thereof for placing a specimen to be observed on the specimen supporting plate.

7 Claims, 6 Drawing Figures

INTEGRATING SPHERE TYPE STANDARD LIGHT SOURCE DEVICE

The present invention relates to an integrating sphere type standard light source device, and more particularly to such a device which is especially useful for observing the brightness and vividness of the color of a metallic powder specimen or an anodized aluminum specimen.

BACKGROUND OF THE INVENTION AND PRIOR ART

In visually inspecting the colors of industrial products, such as those which are coated with paint, plastic materials, colored aluminum and the like, it is often necessary to compare slight differences in colors. Heretofore, inspections of this sort have been conducted under natural daylight, or by means of a standard light source employing an artificial source of light.

For comparing colors under natural daylight, it is recommended that the inspection be carried out during the period from three hours after sunrise to three hours before sunset. The natural daylight during this period varies continually, however, depending upon the season, weather conditions and time, making it difficult to obtain a constant condition. Preferably, therefore, artificial illumination by a standard light source is used for industrial applications.

In conventional standard light-source equipment, the color is visually observed from a position at an angle of 45° to the surface of the specimen while light from a source of light directly above the specimen is directed on the upper portion of the specimen, the source of light being a xenon lamp, a fluorescent lamp having a color temperature of 6500° K. and D65 light characteristics as specified by JIS and CIE (International Committee of Illumination), or a tungsten incandescent lamp.

FIG. 1 shows a conventional example of a simply constructed standard light source device, in which a fluorescent lamp 3 having $D_{65}$ light characteristics is disposed above an illuminating opening in a floor 2 of a light source chamber located in the upper portion of a housing 1, a ground glass plate 4 is mounted in the illuminating opening, a specimen 5 is placed at the center of the bottom surface of the housing 1, and the color is observed through the opening in the front of the housing from the direction of arrow 6 at an angle of about 45° with respect to the surface of the specimen.

The light from the light source 3 is scattered by the ground glass 4. Most of the light illuminating the specimen 5, however, travels in one direction from above the specimen as indicated at 7. If the specimen is observed from an angle of 45° as indicated by arrow 6 under these conditions the light is scattered as indicated at 8, and only the light reflected at the angle of 45° by the surfaces of the specimen 5 enters the eyes, and the light reflected in other directions as designated at 7' does not enter the eyes. Since the fluorescent lamp always illuminates the specimens with a predetermined amount of light so that a predetermined amount of reflected light will enter the eyes, the abovementioned standard light-source device has been so widely used that it has become indispensable for visually inspecting and comparing the colors of products.

Although the described device is very useful for inspecting coated products in general, plastic products, fibrous products and the like, it is not now useful for comparing the colors of automobiles and building materials in which abundant uses are made of metallic coatings and colored oxide-film aluminum which exhibit special visual effects due to the use of such optical characteristics as double reflection consisting of irregular reflection by the surface and directive regular reflection, and polarization. Namely, when such coatings are illuminated by light incident from only one direction as employed in conventional devices, the amount of reflected light entering the eyes, i.e., the color, changes even with a slight change in the relative position of the eyes and the specimen, making it difficult to compare the colors. Therefore, products which have passed inspection carried out by the above-described device often turn out to be defective after shipment.

This is caused by the fact that the light illuminating the specimen is unidirectional, which is different from natural daylight.

The reflection characteristics of a metallic powder coated layer and an anodically oxidized film layer of colored aluminum are shown diagrammatically in FIGS. 2 and 3 and will now be discussed. Referring to FIG. 2, a fine metal powder 12 of a material such as aluminum is dispersed in the upper portion of a transparent resin layer 11 on the metallic coating. Although the reason is not clear, the fine metal powder is oriented in a given direction. If the light 13 is incident from a given direction, the light is reflected from the surface of the resin layer and scattered by the surfaces thereof as at 14 and an intense light 15 is reflected by the oriented fine metallic powder 12 and transmitted through the transparent resin layer 11. Therefore, when viewed from the direction toward which the regularly reflected light 15 is reflected, a glaring color specific to the metallic coating will be seen. This color, however, will not be seen from other angles. In the case of colored aluminum shown in FIG. 3, if the light 21 is incident from a given direction, the light is reflected and scattered by the surfaces of the anodic coating 23 as at 22, and an intense light 25 is reflected by the metallic aluminum and transmitted through the anodically oxidized film layer 23. Therefore, when viewed from the direction toward which the intense reflected light 25 is reflected, a dense and vivid color specific to the colored aluminum will be seen. This color, however, will not be seen from other directions. Further, the phenomenon of polarization develops depending upon the thickness of the anodically oxidized film layer and the kinds of dyestuff. For instance, a yellowish incident light, when reflected, may often be seen as being greenish in color.

On the other hand, under bright daylight i.e., when illuminated from all directions by light irregularly reflected by surrounding buildings and the ground and by light reflected in a scattered manner by dust and dirt in the sky and clouds as a result of the incident sunlight, the observer will invariably see evenly scattered light and evenly reflected intense light reflected by the metallic coating or colored aluminum even when the position of the observer is changed. That is, a color having optical characteristics specific to the coating will be seen. This is the color feeling that people perceive outdoors or indoors from automobiles having metallic coatings and high-rise buildings and the like coated with anodically oxidized colored aluminum.

Therefore, the colors of such products cannot be correctly compared by a conventional standard light-source device which radiates light from one direction only, and differences in color is often not discernible, because only the light that is scattered and directionally reflected is perceived, and the color feeling that would really be created outdoors is not produced. Accordingly, such products which have passed inspection made with such a device are often found to be defective after shipment.

OBJECTS AND BRIEF SUMMARY OF THE INVENTION

It is an object of the present invention to provide an integrating sphere type light source device to overcome the aforementioned defects inherent in the conventional inspection devices of this type, the development of which has lagged behind the technique of surface treatment.

It is a further object to provide an innovative standard light source device in which the illuminating conditions under which a person looks at colors of objects in an outdoor environment (or in a relatively bright room) are artifically reproduced by using close to ideal light from a source of light, such that colors can be compared and differences in colors can be distinguished just as by inspection under natural daylight, no matter how complex the reflection characteristics of the surface layers of the products may be, and in which the color rendering and the fluorescent whitening effects can be compared.

These objects are achieved according to the present invention by the provision of an integrating sphere type standard light source, comprising: a spherical shell having the inner surface coated with a white coating having a high reflectivity, said shell having a light source aperture in the top thereof, a viewing aperture in the side thereof and a specimen exposure aperture in the bottom thereof; a light source means mounted in said light source aperture and depending into said said shell and including a source of light and a light shielding plate between said source of light and the remainder of the interior of said shell, said light shielding plate being coated with a white coating having a high reflectivity; a specimen supporting plate beneath said specimen exposure aperture and normally positioned for supporting a specimen at the bottommost point of an imaginary spherical surface which is an extension of the internal surface of said shell into said specimen exposure aperture; and means on which said specimen supporting plate is mounted for moving said specimen plate into and out of the normal position thereof for placing a specimen to be observed on said specimen supporting plate.

BRIEF DESCRIPTION OF THE DRAWINGS

The invention will now be described more fully in connection with the accompanying drawings in which.

DETAILED DESCRIPTION OF THE INVENTION

Figure 6:
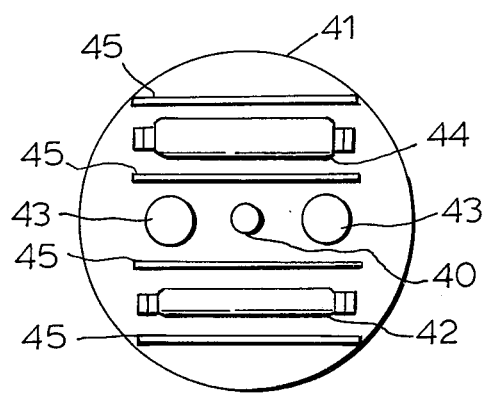
FIG. 6 is a plan view of the light source of the device of FIGS. 4 and 5 showing light-shielding plates arrayed among and on both sides of the lamps that serve as sources of light.

An embodiment of the standard integrating sphere type light source device according to the invention will now be described in detail with reference to FIGS. 4–6.

Figure 1:
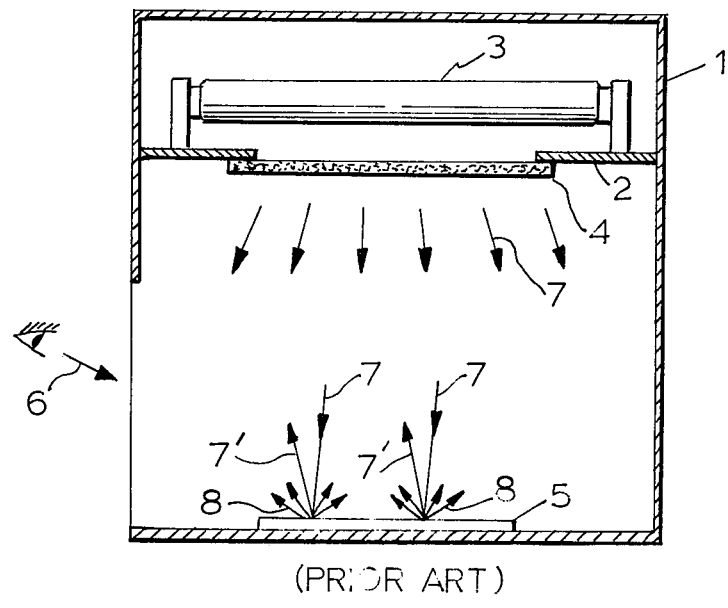
FIG. 1 is a cross-sectional view of a conventional light source device.
Figure 2:
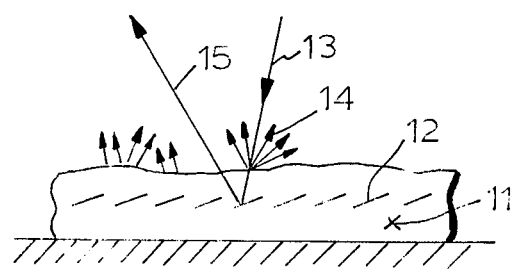
FIG. 2 is a cross-sectional view showing light reflected by a metallic coated layer.
Figure 3:
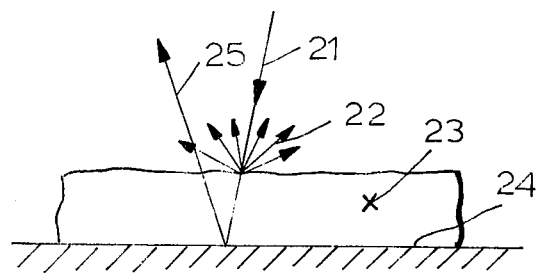
FIG. 3 is a cross-sectional view showing light reflected by an anodically oxidized coating layer of colored aluminum.
Figure 4:
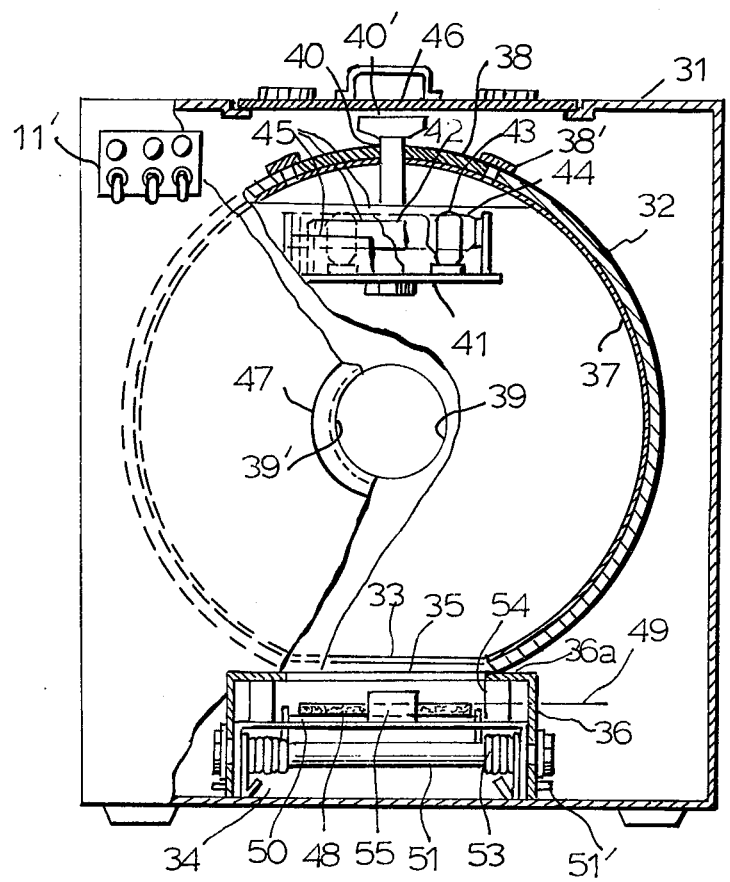
FIG. 4 is a front view, partially broken-away of an integrating sphere type light source device according to the present invention.
Figure 5:
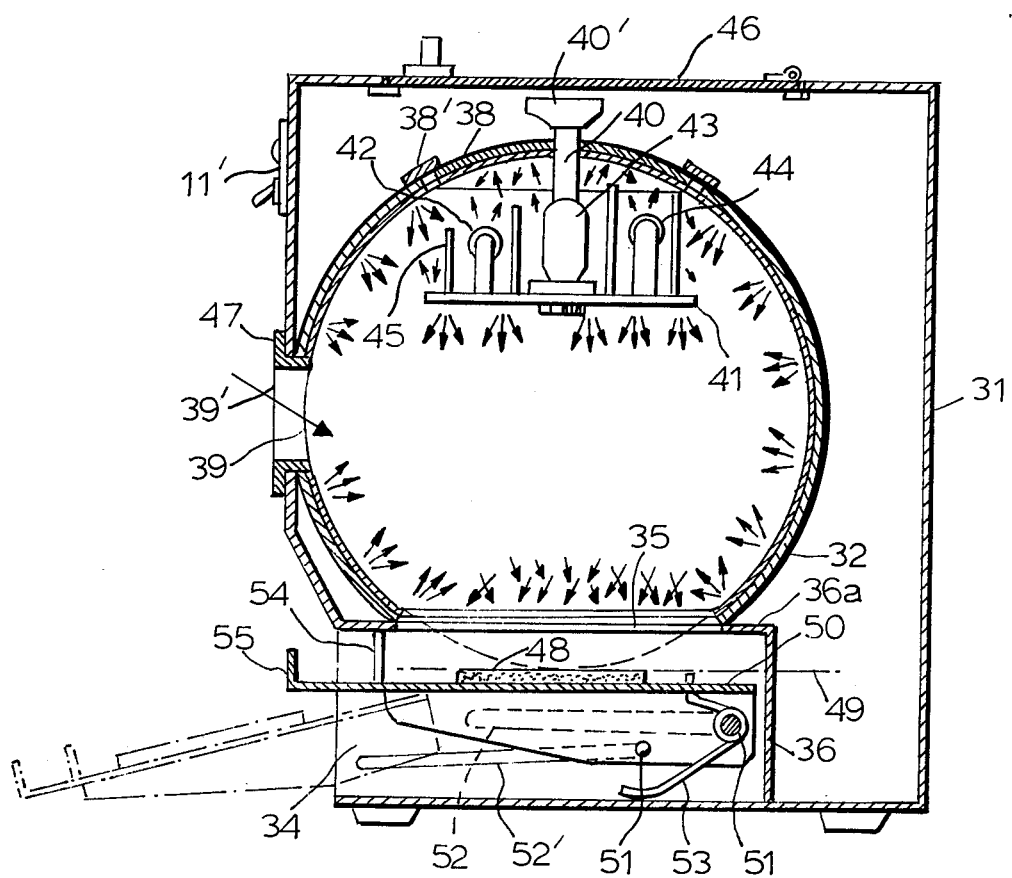
FIG. 5 is a vertical cross-sectional view of the device of FIG. 4.

Referring to FIGS. 4 and 5, a cubic housing 31 for the standard integrating sphere type light source device according to the invention has therein an integrating sphere 32 having a diameter such that it almost completely occupies the space within the housing. The integrating sphere 32 is preferably made of plate material of a light metal, such as aluminum, by draw molding. The integrating sphere 32 has the circumferential portion of a circular illumination hole 33 formed at the lowest portion thereof fixed on the top plate 36a of an integrating sphere mounting base 36 having a specimen introducing port 34 opening through the lower portion of the surface of the housing 31. The top plate 36a has a light transmission hole 35 therein that matches the hole 33.

A white coating layer 37 of a material having high reflectivity, such as barium sulfate having a substantially uniform thickness greater than 1 mm, is provided on the inner surface of the integrating sphere 32.

The top portion 38 of the integrating sphere 32 is a detachable ceiling cover. An annular cover seat 38' is fitted around the circumference of the cover, which is diametrically opposite the illumination hole 33 in the lowest portion. A circular observation hole 39 is provided on one side of the integrating sphere 32 at a position corresponding to the front inner surface of the housing 31.

To the ceiling cover 38 is attached a support pole 40 which extends vertically through the center thereof, and the upper end of the support pole 40 has a grip 40' for lifting the cover. To the lower end of the support pole 40 is attached the central portion of a circular horizontally extending light-shielding plate 41 having a diameter smaller than that of the ceiling cover 38. On the upper surface of the shielding plate 41 are mounted an ordinary $D_{65}$ lamp 42, two tungsten incandescent lamps 43 and a black-light lamp 44. The light-shielding plate 41 blocks direct impingement of light from the sources of light on a specimen placed beneath them. Shields 45 are also provided among the individual sources of light and on both sides of the sources of light, so that when one of the sources of light is selectively turned on by means of a turn-on switch 11' on the front of the housing 31, the emitted light will not directly illuminate the other sources of light (refer to FIG. 6). As is the case with the inner surface of the integrating sphere, a white coating of barium sulfate having a high reflection factor, i.e. nearly 100%, is coated on the entire area of the surfaces of the light-shielding plate 41 and the shields 45.

Therefore, the light from one of the sources of light is first reflected by the while barium sulfate coated surfaces. Further, since the surfaces are coarse surfaces with no luster, the light from the source of light is irregularly reflected in all directions without being absorbed at all in the integrating sphere and is scattered in the integrating sphere. Consequently, the light is uniform in all the space within the sphere. Even if a rod is placed in the sphere, no shade will be developed because the light illuminates it from all directions.

On the upper surface of the housing 31 is provided an openable cover 46 through which the light-shielding plate 41 can be removed together with the ceiling cover 38 when it is desired to replace a source of light. An observation window 39' is located in the central front portion of the housing 31 in alignment with the circular hole 39. The two openings 39 and 39' are connected by means of a mounted fitting ring 47.

A specimen plate 50 is resiliently insertable and removable from the mounting base 36 so that the surface of a specimen 48 to be inspected can be correctly and easily located at a proper level 49 at which the specimen is in a horizontal position at a level corresponding to the bottom of an imaginary spherical surface which is an extension of the internal surface of the integrating sphere 32 in the illuminating hole 33. The ends of a horizontal shaft 51 supporting the rear end of the specimen plate 50 extend through horizontal elongated guide grooves 52 in the right and left side walls of the base 36. The guide grooves 52 guide the shaft 51 so that the specimen plate 50 can be moved laterally through the opening 34 from the normal position in which it supports the specimen 48 at level 49, shown in full lines in FIG. 5, to a withdrawn position, shown in chain lines in FIG. 5, at which a specimen 48 can be easily mounted thereon. A coil spring 53 is attached to both ends of the shaft 51 for resiliently pressing the plate 50 upwardly so that the shaft 51 is against the upper edges of the grooves 52. One end of each coil spring is fixed to the specimen plate 50 and the other end is slidable on and resiliently engaged with the bottom surface of the housing 1. The front edge of the specimen plate 50, i.e. the edge closest to the opening 34, has at both ends projections 54 for resiliently pressing against the lower surface of the top plate 36a, and also has a grip 55 which extends forward from the central portion thereof. There is further provided a projection 51' for restricting the countermovement of the spring when the specimen plate 50 is pulled out of the base 36 and the projection 51' is guided in an elongated groove 52' in the base 36 which extends forward and downward.

When the specimen 48 is observed through the observation window 39' while the upper surface is illuminated with uniform light reflected from the inner surface of the integrating sphere 32 as shown in FIG. 5, the specimen will always have its true color irrespective of whether the specimen has strong reflecting directivity, or even if the specimen is inclined or the position of the eyes is slightly changed. That is to say, the color of the specimen is what it would be if it were observed under conditions of natural daylight.

The two types of reflected light from the specimen, the light irregularly reflected by the surfaces of the metallic coating layer and the light regularly reflected by the metallic powder in a specimen with a metallic powder coated layer, and reflected light consisting of the light irregularly relfected by the surfaces of the anodically oxidized aluminum layer and the light regularly reflected by the aluminum base and passing through the colored layer in an anodically oxidized aluminum specimen, and the color of a specimen having a polarizing property, will be unchanged even when the viewing angle is viewed from the normal viewing angle of 45°, because the light is completely scattered in the integrating sphere and the regularly reflected light travels in the viewing direction as well. Consequently, bright and vivid color will be produced just as when the specimen is looked at in the brightness of daylight.

Therefore, with a light source device according to this invention, it is possible to visually observe the specimens in their true colors without the appearance being affected by a change in the viewing angles within the range of angles at which the specimen can be viewed through the observation windown 39', which effect is impossible with conventional light source devices.

Below are described experimental results of observations of colors of specimens using a conventional light source device and the light source device of this invention, in comparison with the results of observations made under daylight conditions.

The observation conditions were as listed in Table 1 below.

TABLE 1

|  | Conventional light source device | Light source device of this invention | Daylight |
|---|---|---|---|
| Source of light | Lamp for $D_{65}$ light source | Lamp for $D_{65}$ light source | Daylight ($D_{65}$ distributed) |
| Illuminating condition | Illuminated from one direction | Completely scattered illumination | Blue-sky scattered light |
| Angle of eyes of observer | At an angle of 45° | At an angle of 45° | At an angle of 45° |

The specimens, which were colored aluminum, were visually observed in comparison with coated plates having no luster and no directivity of reflection as representative examples of general colors.

(1) Comparison of the brightness of the specimens:

Five colored aluminum specimens were observed using the conventional light source device, the light source device of this invention, and under the daylight condition. The order of brightness during observation of the specimens, with the brightness decreasing from 1-5, is shown in Table 2, and the order of brightness during observation of three coated plates having no luster and no directivity of reflection is shown in Table 3.

TABLE 2

| Color of colored aluminum specimen | Conventional light source | Light source of this invention | Daylight |
|---|---|---|---|
| Dark blue | Order 3 | Order 5 | Order 5 |
| Pale Blue | 5 | 3 | 3 |
| Yellow | 2 | 1 | 1 |
| Yellowish red | 1 | 2 | 2 |
| Red | 4 | 4 | 4 |

TABLE 3

| Color of coated plate | Convention light source | Light source of this invention | Daylight |
|---|---|---|---|
| Blue | Order 3 | Order 3 | Order 3 |
| Yellow | 1 | 1 | 1 |
| Red | 2 | 2 | 2 |

From these observations, it can be seen that although the brightness of the coated plates having no luster and no directivity of reflection observed under both the conventional light source and that of the present invention were in agreement with those observed under the daylight condition, the brightness of the colored aluminum specimens observed under the conventional light source device differed from those observed under daylight. However, the order of brightness, when the specimens were observed using the light source device of this invention correspond with those observed under daylight. Referring to Table 2, for instance, the dark blue color of the specimen had an order of brightness of 5 when it was observed using the light source device of this invention and was thus in agreement with that observed under the daylight. When observed using the conventional light source device, however, the order of brightness was 3 which was not in agreement with that observed under the daylight.

This indicates that the colored aluminum cannot be properly examined with a conventional light source device. The light source device of this invention, on the other hand, makes it possible to examine the specimens and obtain valid results.

(2) Comparison of vividness of the specimens:

In examining a specimen for vividness of the color, colors of the specimens are usually visually observed with reference to colors of standard samples which have been prepared beforehand. Standard samples in the form of coated plates of hues of the colors of the specimens were therefore prepared using a color chart and which had no directivity of reflection and on a chroma scale consisting of five grades by changing the vividness little by little in the same hue from a high degree of chroma to a low degree of chroma. Observation of the five colored alumimun specimens and the standard samples which had no luster or directivity of reflection, gave the results that are shown in Tables 4 and 5 below. The chroma scale was divided into five grades, i.e., 1, 2,–5, starting from the lowest grade of chroma, and the highest grade of chroma was denoted by the grade 5. The vividness of the specimens were observed using each of the light sources to determine the grade of chroma of the specimens.

TABLE 4

| Color of colored aluminum specimen | Conventional light source | Light source of this invention | Daylight |
| --- | --- | --- | --- |
| Dark blue | Grade 2 | Grade 4 | Grade 4 |
| Pale blue | 3 | 5 | 5 |
| Yellow | 3 | 5 | 5 |
| Yellowish red | 3 | 5 | 5 |
| Red | 1 | 3 | 3 |

TABLE 5

| Color of coated plate standard sample | Conventional light source | Light source of this invention | Daylight |
| --- | --- | --- | --- |
| Blue | Grade 3 | Grade 3 | Grade 3 |
| Yellow | 3 | 3 | 3 |
| Red | 4 | 4 | 4 |

For the coated plate standard samples having no luster and no directivity of reflection, the chroma grades observed under the two light source devices were in agreement with those observed under the daylight condition. For the colored aluminum specimens, however, the chroma grades observed using the conventional light source were not in agreement with those observed under the daylight condition. Using the light source device of this invention, however, the chroma grades of the colored aluminum specimens were in agreement with those observed under the daylight condition. With reference to Table 4, for instance, the dark blue had a chroma grade of 4 under the light source device of this invention and was in agreement with the grade determined under the daylight condition. This color, however, had a grade of 2 under the conventional light source device, which was not in agreement with the grade determined under the daylight condition; when using the conventional light source device, the chroma grade appeared to be shifted toward the lower grades, and the true vividness appeared to be lacking.

As described above, with the conventional light source device, the brightness and vividness of the colored aluminum specimens appear differently than what is usually seen under the daylight conditions. Therefore, using the conventional light source device, the observation of the brightness and vividness of colors gives incorrect results. Using an integrating sphere type standard light source device according to this invention, on the other hand, makes it possible to obtain correct results the same as when the colors are seen in daylight conditions.

What is claimed is:

1. An integrating sphere type standard light source, comprising: a spherical shell having the inner surface coated with a white coating having a high reflectivity, said shell having a light source aperture in the top thereof, a viewing aperture in the side thereof and a specimen exposure aperture in the bottom thereof; a light source means mounted in said light source aperture and depending into said shell and including a source of light and a light shielding plate between said source of light and the remainder of the interior of said shell, said light shielding plate being coated with a white coating having a high reflectivity; a specimen supporting plate beneath said specimen exposure aperture and normally positioned for supporting a specimen at the bottommost point of an imaginary spherical surface which is an extension of the internal surface of said shell into said specimen exposure aperture; and means on which said specimen supporting plate is mounted for moving said specimen plate into and out of the normal position thereof for placing a specimen to be observed on said specimen supporting plate.

2. An integrating sphere type standard light source as claimed in claim 1 in which said white coating is barium sulfate.

3. An integrating sphere type standard light source as claimed in claim 1 in which said light source means further comprises a cover fitting over said light source aperture, said light shielding plate being spaced inwardly of said shell from said cover and a pole connected between said cover and said shielding plate, said source of light being on the upper surface of said shielding plate.

4. An integrating sphere type standard light source as claimed in claim 3 in which said cover has a handle on the top thereof.

5. An integrating sphere type standard light source as claimed in claim 1 in which said source of light comprises a plurality of lamps each emitting a different type of light, and light shields on said light shielding plate between respective ones of said lamps, said light shields being coated with a white coating having a high reflectivity.

6. An integrating sphere type standard light source as claimed in claim 5 in which said lamps are a $D_{65}$ lamp, a tungsten incandescent lamp, and a black light lamp.

7. An integrating sphere type standard light source as claimed in claim 1 in which said viewing aperture is at the end of a diametrical axis of said sphere which is perpendicular to a diametrical axis between said light source aperture and said specimen exposure aperture.

* * * * *